(12) United States Patent
Duveen et al.

(10) Patent No.: US 11,103,668 B2
(45) Date of Patent: Aug. 31, 2021

(54) HUMIDIFICATION FACE MASK

(71) Applicant: Humid Med Technology (Pty) Ltd, Cape Town (ZA)

(72) Inventors: Justin Marc Duveen, Cape Town (ZA); Jacobus Terblanche, Cape Town (ZA)

(73) Assignee: Humid Med Technology (PTY) LTD, Cape Town (ZA)

( * ) Notice: Subject to any disclaimer, the term of this patent is extended or adjusted under 35 U.S.C. 154(b) by 674 days.

(21) Appl. No.: 15/381,156

(22) Filed: Dec. 16, 2016

(65) Prior Publication Data

US 2017/0119991 A1  May 4, 2017

Related U.S. Application Data

(62) Division of application No. 13/141,879, filed as application No. PCT/IB2009/007695 on Dec. 9, 2009, now abandoned.

(30) Foreign Application Priority Data

Jan. 11, 2009 (ZA) ................................. 2008/06035
Nov. 26, 2009 (ZA) ................................. 2009/08408

(51) Int. Cl.
*A61M 16/16* (2006.01)
*A61M 16/10* (2006.01)
(Continued)

(52) U.S. Cl.
CPC ..... *A61M 16/1045* (2013.01); *A41D 13/1138* (2013.01); *A61M 16/06* (2013.01);
(Continued)

(58) Field of Classification Search
CPC ..... A41D 13/05; A41D 13/11; A61M 16/047; A61M 16/10; A61M 16/1055;
(Continued)

(56) References Cited

U.S. PATENT DOCUMENTS 3,326,214 A  6/1967  McCoy
3,620,214 A  11/1971 Thackston
(Continued)

FOREIGN PATENT DOCUMENTS

JP   H2-274265    11/1990
JP   H10-118183   5/1998
JP   2006-122268  5/2006

*Primary Examiner* — Annette Dixon
(74) *Attorney, Agent, or Firm* — Nelson Patent Law

(57) ABSTRACT

A self-contained re-humidification mask that can be supported in an operative position on a user is provided. The mask has a wall shaped as a moulded domed mask configured to cover the face of a user from the nose to the chin. An endless peripheral edge is shaped and configured to generally anatomically follow the contours of a face of a user to define, with the face of a user, an air pocket. The mask has a single inlet-outlet aperture located generally opposite a position occupied in use by a mouth of a user, and at least one re-humidification assembly located in the inlet-outlet aperture such that it substantially fills the aperture. The re-humidification assembly includes a coil of corrugated hygroscopic paper having an axis of the coil extending in the direction of fluid flow through the inlet-outlet aperture. The re-humidification mask preferably has a wall formed from a non-woven synthetic fibre sheet that is press moulded and heat set to the domed shape.

2 Claims, 4 Drawing Sheets

(51) Int. Cl.
*A61M 16/06* (2006.01)
*A62B 9/00* (2006.01)
*A41D 13/11* (2006.01)
*A62B 18/02* (2006.01)
*A62B 23/02* (2006.01)

(52) U.S. Cl.
CPC ...... *A61M 16/0683* (2013.01); *A61M 16/106* (2014.02); *A62B 9/003* (2013.01); *A62B 18/02* (2013.01); *A62B 23/025* (2013.01); *A61M 16/107* (2014.02); *A61M 16/1055* (2013.01)

(58) Field of Classification Search
CPC ..... A61M 16/16; A61M 16/162; A62B 23/00; A62B 23/02; A62B 9/00
See application file for complete search history.

(56) References Cited

U.S. PATENT DOCUMENTS

| | | | |
|---|---|---|---|
| 4,136,691 A | 1/1979 | Ebeling et al. | |
| 4,458,679 A | 7/1984 | Ward | |
| 4,620,537 A * | 11/1986 | Brown | A62B 18/025 128/201.13 |
| 4,807,619 A | 2/1989 | Dyrud et al. | |
| 4,856,508 A | 8/1989 | Tayebi | |
| 4,873,972 A | 10/1989 | Magidson et al. | |
| 4,883,052 A | 11/1989 | Weiss | |
| 4,941,467 A | 7/1990 | Takata | |
| 5,007,114 A | 4/1991 | Numano | |
| 5,022,394 A * | 6/1991 | Chmielinski | A61M 16/1045 128/206.17 |
| 5,080,094 A | 1/1992 | Tayebi | |
| 5,094,236 A | 3/1992 | Stern et al. | |
| 5,143,061 A * | 9/1992 | Kaimer | A41D 13/1146 128/205.25 |
| 5,316,601 A | 5/1994 | Hebbard et al. | |
| 5,372,130 A | 12/1994 | Stern et al. | |
| 5,433,192 A * | 7/1995 | Ebeling | A41D 13/11 128/201.13 |
| 5,435,299 A | 7/1995 | Langman | |
| 5,460,172 A * | 10/1995 | Eckerbom | A61M 16/1045 128/201.13 |
| 5,570,684 A | 11/1996 | Behr | |
| 5,595,173 A | 1/1997 | Dodd, Jr. | |
| RE36,165 E | 3/1999 | Behr | |
| 5,884,336 A | 3/1999 | Stout | |
| 6,375,724 B1 | 4/2002 | Foti | |
| 6,763,835 B1 | 7/2004 | Grove | |
| 8,733,357 B2 | 5/2014 | Sullivan, Jr. | |
| 2005/0248045 A1 * | 11/2005 | Anthony | A61M 16/16 261/154 |
| 2010/0024826 A1 | 2/2010 | Sullivan | |

* cited by examiner

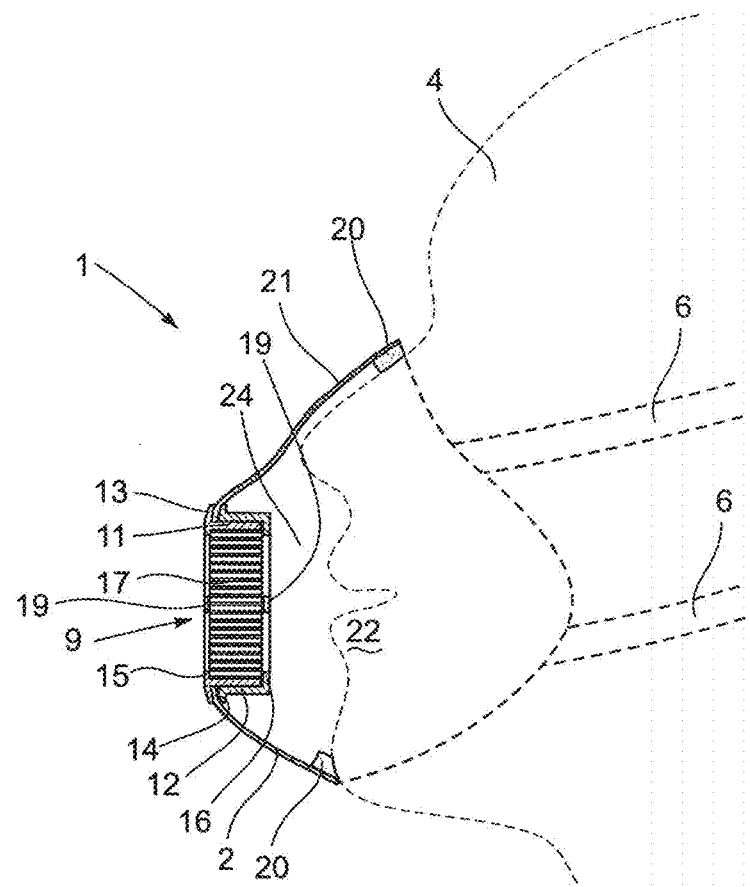

HUMIDIFICATION FACE MASK

CROSS REFERENCE TO RELATED APPLICATIONS

This application is a divisional application of U.S. application Ser. No. 13/141,879, filed Jun. 23, 2011 [now abandoned], which is a National Stage application of International Application Number PCT/IB2009/007695, filed Dec. 9, 2009; which claims priority to South Africa Application Nos. 2008/06035, filed Jan. 11, 2009 and 2009/08408, filed Nov. 26, 2009; the disclosures of each of which are incorporated herein by reference in their entirety, including any figures, tables, and drawings.

FIELD OF THE INVENTION

This invention relates to improvements in self-contained humidification face masks. More particularly the invention relates to self-contained re-humidification face masks that operate independently of any respirator equipment.

BACKGROUND TO THE INVENTION

Painful conditions, such as recovering after nasal surgery or surgery requiring intubation and other trauma to the nose, mouth and throat are rendered more painful by breathing within a dried and cold air environment such as in an air conditioned room.

Furthermore, travelling in a dry and cold air environment, such as that of an aircraft, may facilitate the development of painful conditions of the nose and throat or aggravate existing conditions. The difficulty of breathing through generally blocked sinuses is also aggravated by exposure to dry and cold air and it has been found that a dry air environment increases the likelihood of infection of the internal passages of the nose and throat. Therefore, exposure to a dry air environment for extended periods of time not only exacerbates the pain of surgical trauma to the nose and mouth of a patient and inhibits the healing thereof, but also promotes the infection of the healthy nose and throat of a traveller. Similar comments apply to those with or recovering from colds and flu particularly when breathing through the mouth is inevitable especially whilst sleeping.

Furthermore, medical and industrial workers are increasingly required to wear masks not only to prevent them from contaminating patients, food, and/or medical equipment, but also to protect them from airborne disease. Thus medical and industrial workers are required to wear protective face masks for extended periods of time, often while working in air-conditioned or otherwise dry air environments. Many masks currently used by workers incorporate low flow rate bacterial and/or viral filters which, while preventing the passage of microbes through the filter, are difficult and uncomfortable for a user to breathe through. Furthermore, with time and the build up of humidity from the user's breath, the integrity and therefore filtering efficiency of the filters become compromised and unreliable.

One type of face mask specifically contemplating the humidification of the breathing air environment makes use of the inclusion of a moisturizing pad that is typically saturated with water before use such that in use the air adjacent the pad is moisturized to provide a humidifying effect to air inhaled through the face mask. This type of face mask is described in U.S. Pat. Nos. 4,941,467 and 6,375,724 and requires the pad to be saturated or charged with an external source of preferably sterile moisture prior to use of the face mask. The retention of this externally sourced moisture within the vicinity of the face of the user for extended periods of time introduces the possibility of contamination of the moisture pad, as the pad remains continually wet for a period of time during both exhalation and inhalation. A further difficulty associated with the use of this type of face mask often includes the gradual cooling of the moisture pad during use such that although the air to be inhaled is moisturized, it is not significantly warmer than that of the ambient air, particularly in relatively colder air environments.

Another type of face mask such as that described for example in USRE36165EE1 is contemplated to be useful in cold weather for the heating and humidifying of inhaled air with previously exhaled air by passing the air through a highly efficient heat exchanger disposed within the mask. This heat exchanger is made up of a multitude of layers of metallic mesh through which the warm exhaled air passes, heating up the mesh which in turn heats up the incoming air before it is inhaled. Moisture from the exhaled air then condenses on the relatively cooler heat exchanging metallic mesh and humidifies the incoming air. However, this device is designed for repeated use and it is an object of this device to provide a humidification device that can be safely washed or sterilized even in a dish washer.

U.S. Pat. No. 5,595,173 describes a re-humidification device that includes a container having a continuous strip of filter paper helically rolled so as to entirely fill the space defined by a cross section of the container. This re-humidification device is however adapted to fit flight masks which deliver pressurized respiratory fluids to a user, and is for this reason connected via various conduits to pressurized respiratory fluids.

The use of several of the face masks listed above is not suited for patients that have undergone nasal surgery. Not only are these masks painful and difficult for a user to comfortably wear during sleep but they become uncomfortably hot to wear after extended periods of use and may not maintain satisfactory engagement with the face of the user during sleep. These masks are also not suited for use by frequent travellers, as they are bulky and inconvenient to carry while travelling. Not only are such masks expensive to manufacture on a large scale for disposable use, but security personnel may prevent travellers from using masks having wire or metal mesh incorporated therein.

Definitions

In the context of this specification the term "re-humidification mask" means a mask that extracts moisture from exhaled air and releases at least some of this moisture by evaporation into inhaled air.

The term "self-contained" means that the mask operates in the absence of a separate supply of moisture such that humidification of inhaled air occurs by re-humidification.

Object of the Invention

It is an object of this invention to provide an alternative humidification face mask which will operate more efficiently than those currently available and will, at least partially, alleviate one or more of the problems mentioned above.

SUMMARY OF THE INVENTION

In accordance with the invention there is provided a self-contained re-humidification mask having locating means to enable the mask to be supported in an operative position on a user, the mask having a wall shaped as a moulded domed mask configured to cover the face of a user from the nose to the chin, the mask having an endless peripheral edge shaped and configured to generally anatomically follow the contours of a face of a user such that, in use, the domed shape of the mask defines, with the face of a user, an air pocket, the mask having a single inlet-outlet aperture located generally opposite a position occupied in use by a mouth of a user, and at least one re-humidification assembly located in the inlet-outlet aperture such that it substantially fills the aperture and is in open communication with the mouth and nose of the user and defines a fluid flow passage between the atmosphere and the air pocket, wherein the re-humidification assembly includes a coil of corrugated hygroscopic paper having an axis of the coil extending in the direction of fluid flow through the inlet-outlet aperture.

A further feature of the invention provide for the inlet-outlet aperture to be defined by a squat tubular holder composed of an inner sleeve and an outer sleeve with each sleeve having an outwardly directed flange at one end thereof with the periphery of a hole cut in the mask wall extending between the two flanges so as to support the tubular holder in the mask and wherein the inner and outer sleeves have formations for holding the re-humidification assembly captive within the tubular holder.

Still further features of the invention provide for the mask wall to be formed from a non-woven synthetic fibre sheet that is press moulded and heat set to the domed shape thereof and wherein the inlet-outlet aperture is located in a hole cut from the mask wall; for the non-woven synthetic fibre sheet to contain relatively low and high melting fibres and the press moulding is carried out at a temperature selected to cause the low melting fibres to trap the high melting fibres in the final shape of the wall and wherein the final wall is gas permeable, at least to a limited extent; and for the domed mask to be moulded from a non-woven sheet of synthetic fibres having a weight of from 100 to 150 g/m$^2$ with the press moulding being carried out to provide a wall thickness in the range of 0.5 to 3.0 mm, preferably about 1.0 mm.

The mask preferably has an endless contoured peripheral edge that is generally non-planar and configured to yieldingly engage the face of a user with the mask being suitably rigidly flexible or pliable to provide a suitable yielding characteristic. It is also preferred that the peripheral edge of the mask has a soft, generally resilient, endless gasket formation for engagement with a user's face. The gasket formation is typically of open or closed cell foam material such as a suitable polyurethane foam or the like.

The diameter of the re-humidification assembly is typically within the range of 10 to 80 mm and preferably within the range of 25-45 mm. The corrugation height of the corrugated hygroscopic paper is preferably within the range of 0.1 to 2.5 mm and preferably about 0.5 mm. The re-humidification assembly may have an axial dimension in the range of 8 to 25 mm preferably about 12 mm.

In one variation of the invention the re-humidification assembly may include a particle filter including electrostatic material which may be suitable for the filtering of bacteria and/or viruses. It may be made to be suitable for the filtering of microbes in compliance with any required standard such as the N95, EN149, or FFP3 standards or lower. The particle filter may be impregnated with antibacterial and/or antiviral medication such as silver nitrate.

In another variation of the invention the re-humidification assembly may include a pad impregnated with a medication. The medication may be at least one essential oil such as menthol oil and a container thereof may be frangible such that the mask may be impregnated with the medication by a user. The container containing the medication may be an accessory capable of clipping or screwing onto the re-humidification mask. A re-humidification mask may be packaged together with a container containing medication for use in impregnating a pad of the mask.

The re-humidification assembly may include hygroscopic paper such as that sold as a Humid-Vent Filter Light HMEF, cellulose paper, or the like.

In order that the invention may be more fully understood one embodiment and some variations thereof will now be described with reference to the accompanying drawings.

BRIEF DESCRIPTION OF THE DRAWINGS

In the drawings: —

FIG. 5 is a sectional side view of the re-humidification mask illustrated in FIG. 1, in use;

FIG. 6 is a rear elevation of the re-humidification mask showing the inside thereof;

DETAILED DESCRIPTION WITH REFERENCE TO THE DRAWINGS

Figure 1:
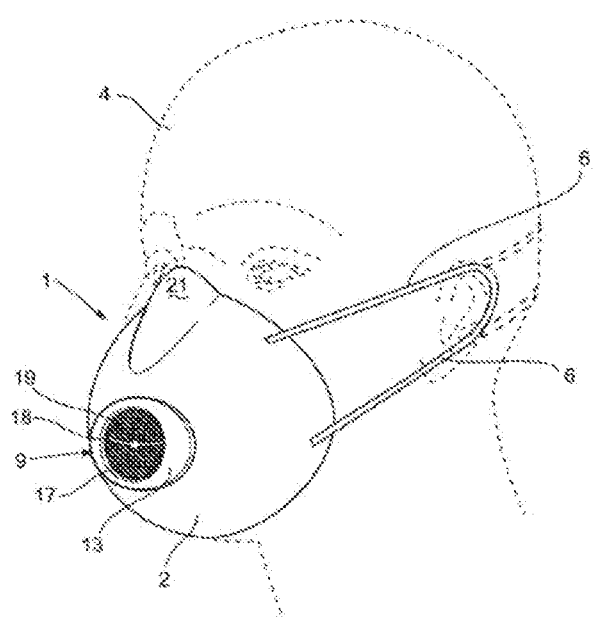
FIG. 1 is a perspective view of one embodiment of re-humidification mask according to the invention illustrated in relation to a user's head that is shown in ghosted lines.
Figure 2:
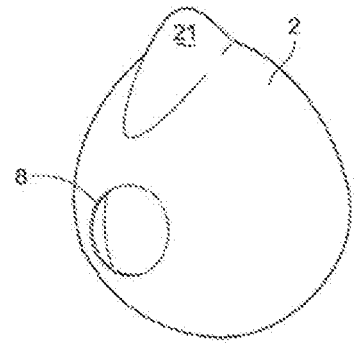
FIG. 2 is a perspective view of a blank mask wall moulded and ready for receiving a re-humidification assembly in order to form the re-humidification mask illustrated in FIG. 1.
Figure 3:
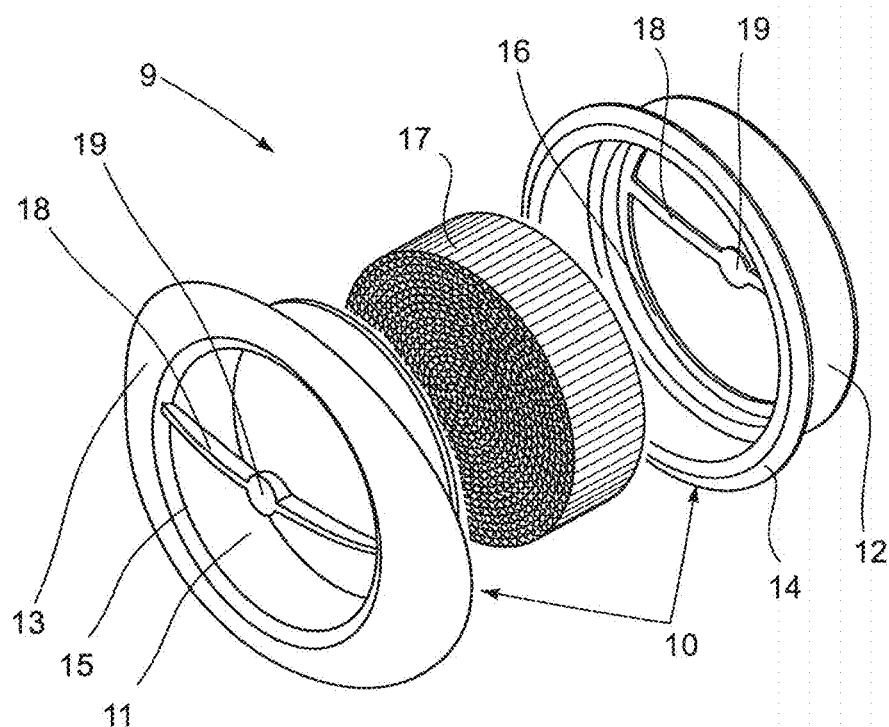
FIG. 3 is an exploded view of the re-humidification assembly of the embodiment of the invention illustrated in FIG. 1.

In the embodiment of the invention illustrated in the drawings, a disposable, self-contained re-humidification mask, generally indicated by numeral (1), has a moulded, domed gas-permeable mask wall (2) of the type configured to be fitted over the nose and mouth of a user (4) and to extend from the nose to the chin. The mask is to be held in place by straps (6) that preferably hook around the ears of the user. The straps could, of course, also extend around the back of the head, the exact configuration being irrelevant to the present invention. The straps may be made of any suitable material and may even be lycra or other hypoallergenic material.

The mask wall (2) is preferably press moulded to form a stiffened but rigidly flexible or pliable and thus suitably yieldable, gas-permeable wall preferably having a wall thickness of about 1.0 mm. The synthetic fibrous sheet material from which the mask wall (2) is press moulded has intermixed fibres of different melting temperatures. A first thermoplastic fibre has a higher melting temperature than a second thermoplastic fibre and the mask wall (2) is moulded by pressing and heating the composite non-woven fibres in a mould to a temperature between that of the two melting temperatures of the constituent thermoplastic fibres.

The lower melting fibre therefore melts and binds the first thermoplastic fibre Such that, upon cooling, the sheet is set in the desired shape of the mask wall (2) whilst remaining gas permeable. The fibres may include polyethersulphone (PES) fibres and the sheet may have a weight of about 120 g/m and a thickness before moulding in the range of 2.4-3.2 mm. Typically, multiple masks will be moulded at one time from a single sheet and the mask walls will be cut from the processed sheet.

At the time of cutting the mask wall from the sheet, a hole (8) is simultaneously cut in the mask wall for receiving the re-humidification assembly generally indicated by numeral (9).

The hole receives a squat tubular holder (10) composed of an inner sleeve (11) and an outer sleeve (12) with each sleeve having an outwardly directed flange (13, 14) at one end thereof, the outer end in this instance, such that the periphery of the hole cut in the mask wall extends between the two flanges and is clamped between them. The inner and outer sleeves may frictionally engage each other to remain in their operative positions; they may clip into a cooperating position; or they may be adhesively secured together. The arrangement is such that the edge of the mask wall supports the tubular holder in the mask.

The inner and outer sleeves also have formations in the form of inwardly directed flanges (15, 16) at opposite ends of the tubular holder for holding a coil (17) of corrugated hygroscopic paper of the re-humidification assembly captive within the tubular holder. The inner and outer sleeves each have a diametrically extending retainer (18) to retain the coil in its operative position with a central enlargement (19) that operatively obscures the axial hole inherently formed at the very centre of the coil.

The hygroscopic paper, in this instance, includes reconstituted hygroscopic paper product. The humidifying assembly (9) may be a Humid-Vent Filter Light HMEF (Gibeck; Upplands Vaesby, Sweden) or the like. In this instance, the operative diameter of the humidifying assembly is 35 mm; the corrugation height 0.5 mm; and the axial dimension of the humidifying assembly is 10-12 mm. Of course, the humidifying assembly is typically of low respiratory resistance. Clearly, the axis of the coil extends in the direction of fluid flow through the inlet-outlet aperture.

The mask has an endless contoured peripheral edge that is generally non-planar and configured to yieldingly engage the face of a user with the mask being suitably rigidly flexible to provide a suitable yielding characteristic. This peripheral edge of the mask has a soft, generally resilient, endless gasket (20) typically of open or closed cell foam material such as a suitable polyurethane foam for engagement with a user's face.

A radially outwardly extending recess (21) is moulded into, and intersects, the operatively upper endless peripheral edge of the mask wall (2) for accommodating the bridge of the nose and thereby enclosing the nose of a wearer.

The arrangement is such that, in use, the humidifying assembly (9) is located opposite and in open communication with the mouth of the user (4). The humidifying assembly (9) is therefore positioned substantially in the centre of the rounded dome of the mask wall (2).

In use, the mask (1) is positioned on the face of the user (4) over the mouth and nose by enclosing the mouth and the bridge of the nose, part of the cheeks and part of the chin of the user (4) within the mask. The mask (1) is urged to yieldingly engage the face and is spaced therefrom to define an air pocket (24) between the face of the user and the mask wall (2). The mask wall (2) is moulded such that, in use, the lips (22) of the user (4) cannot contact the humidifying assembly (9).

In use, exhaled air passes through the re-humidification assembly and, in so doing, relinquishes heat and moisture to the highly absorbent re-humidification assembly. Inhaled air, on the other hand, becomes warmed somewhat and humidified by the absorbed heat and moisture carried temporarily by the re-humidification assembly.

As indicated above, the re-humidification assembly may further include a planar particle filter (25) including electrostatic material and selected so as to be suitable for the filtering of selected particles, in particular, microbes such as bacteria and viruses in compliance with N95, EN149, and/or FFP3 regulation standards. This particle filter may be located adjacent the coil of corrugated hygroscopic paper (17) within the re-humidification assembly (9).

Figure 4:
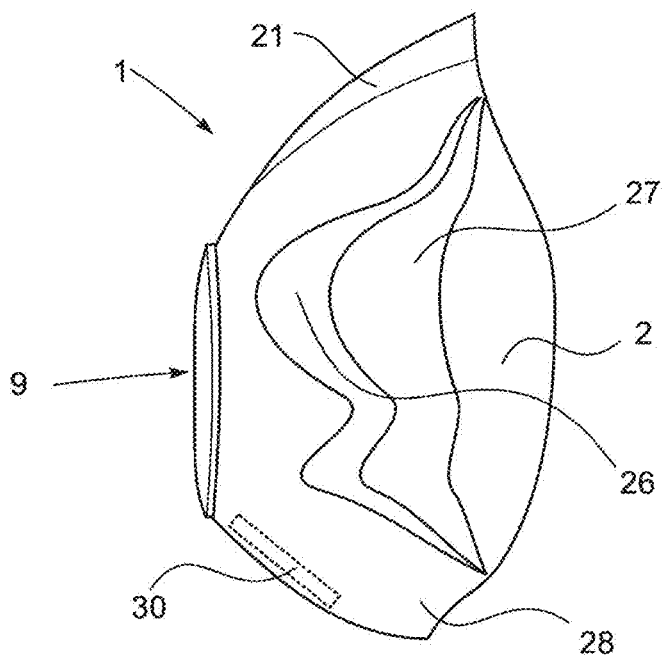
FIG. 4 is a side view of the re-humidification mask illustrated in FIG. 1.
Figure 7:
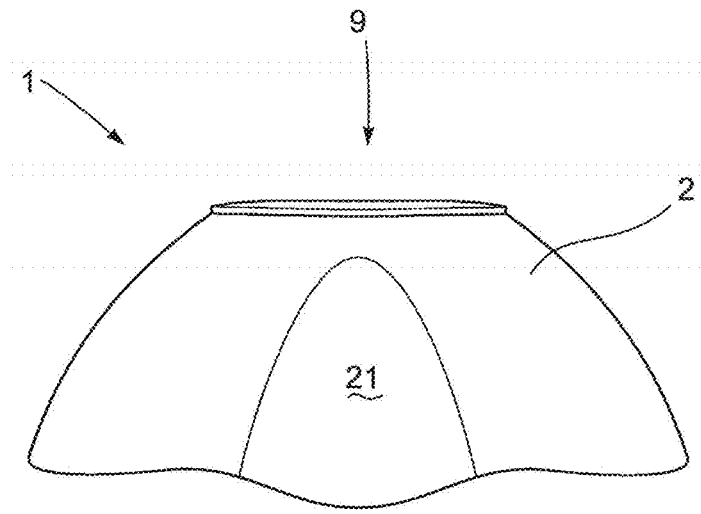
FIG. 7 is a view from the top thereof.
Figure 8:
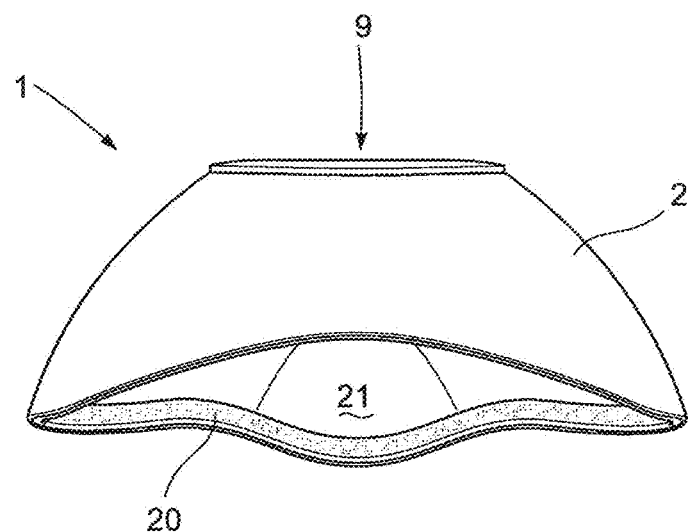
FIG. 8 is a view from the bottom thereof.

As indicated in FIG. 4, the domed mask may be multi-layered and may include an outside layer (26) of electrostatic material suitable for the filtering of microbes such as bacteria and viruses. A layer (27) of hydrophobic material may be layered on the inside surface of the mask over the gas-permeable material layer such that the electrostatic material layer is protected from the humidity of the user's breath. Alternatively, this hydrophobic layer may be positioned between the outer electrostatic layer and the inner gas-permeable layer. A further layer (28) of printable material may be added to the outside of the mask for aesthetic or promotional purposes.

It will be appreciated that many additional features may be added to the re-humidification mask (1) of the invention. Such features may include the use of a pad (30) which may be impregnated with medication Such as menthol oil and located in or around the humidifying assembly (9) on the interior of the re-humidification device (1). A kit may be provided which includes a self-contained re-humidification device of the invention, a frangible container containing medication, and a pad. The medication-impregnated pad may then be inserted or clipped onto the mask.

The dome of the re-humidification mask of the invention defines an air pocket between the mask and the face of the user that is relatively greater than that provided currently on competitive devices. The humidifying assembly of the device of the invention is therefore relatively more remote from the mouth and nose of the user than is the humidifying assembly of currently available devices.

The re-humidification mask of this invention may be comfortably worn during sleep. It is especially notable that the soft yet pliable mask and the soft resilient gasket material in combination with the non-elastic straps make for a most comfortable experience. The mask has no protruberances that could possible function as a source of discomfort or even injury.

Furthermore, unlike currently available masks, the mask of this invention may be made to be both disposable and self-contained without requiring an external source of pressurized air, moisture and conduits associated therewith. It can be made to be biodegradable in keeping with modern tendencies. The self-contained nature of the mask of the invention allows for greater ease and application of use. The invention is also relatively cheaper to produce than re-humidification masks that are currently available.

Importantly, in comparison to currently available masks, the re-humidification mask of the invention has a high flow rate making it easier for a user to breathe whilst wearing same. The mask provided by this invention may therefore be worn over prolonged periods of time, helping a user to recover from surgical procedures or whilst travelling on an aircraft or recovering from any ailment involving a blocked nose and consequent breathing through the mouth.

Furthermore, the hygroscopic nature of the corrugated coil of paper in the mask of the invention may function as a desiccant, wicking accumulated moisture away from any bacterial and/or viral filter incorporated into the mask, thereby extending the filtering efficiency and lifespan of the bacterial and/or viral filter.

The invention claimed is:

1. A self-contained re-humidification mask capable of being supported in an operative position on a user, the mask having a wall shaped as a moulded domed mask configured to cover the face of a user from the nose to the chin, the mask comprising:
   an endless peripheral edge shaped and configured to generally anatomically follow the contours of a face of a user such that, in use, the domed shape of the mask defines, with the face of the user, an air pocket;
   a single inlet-outlet aperture located generally opposite a position occupied in use by a mouth of a user, and at least one re-humidification assembly located in the inlet-outlet aperture such that it substantially fills the inlet-outlet aperture and is in open communication with the mouth and nose of the user and defines a fluid flow passage between the atmosphere and the air pocket, wherein said inlet-outlet aperture comprises an inner sleeve and outer sleeve, such that the inner and outer sleeves may frictionally engage each other to retain their operable position; and
   a layer of hydrophobic material layered on the inside surface of said mask;
   wherein the re-humidification assembly comprises:
      a coil of corrugated hygroscopic paper having an axis of the coil extending in the direction of fluid flow through the inlet-outlet aperture, a coil retainer with a central enlargement operable to obscure an axial hole at the center of said coil, and
      an electrostatic particle filter located adjacent the coil within the re-humidification assembly,
   such that exhaled air passes through the re-humidification assembly and, in doing so, relinquishes heat and moisture to the corrugated hygroscopic paper of the re-humidification assembly and inhaled air is warmed and humidified by absorbed heat and moisture carried temporarily by the corrugated hygroscopic paper of the re-humidification assembly.

2. A self-contained, dome shaped, re-humidification face mask comprising:
   a mask wall operable to engage a wearer's face with a soft gasket, extending from nose to chin and enclosing the nose and mouth of said wearer within a pocket of air;
   an inlet-outlet aperture formed within said face mask, said inlet-outlet aperture being in open communication with the mouth of the wearer, said inlet outlet aperture having a tubular holder, wherein said tubular holder comprises an inner sleeve and outer sleeve, such that the inner and outer sleeves may frictionally engage each other to retain their operable position;
   a coil of corrugated hygroscopic paper having an axis of the coil extending in the direction of fluid flow through said inlet-outlet aperture when mounted within said tubular holder, the tubular holder having a coil retainer with a central enlargement operable to obscure an axial hole at the center of said coil; and
   whereby heat and humidity in air exhaled from the wearer's mouth and nose is received and retained by said coil of corrugated hygroscopic paper, then returned to air within the face mask upon inhalation.

* * * * *